US00PP37541P2

(12) United States Plant Patent
Stewart et al.

(10) Patent No.: US PP37,541 P2
(45) Date of Patent: Jul. 28, 2026

(54) STRAWBERRY PLANT NAMED 'DrisStrawOneHundredThirteen'

(50) Latin Name: *Fragaria x ananassa*
Varietal Denomination: DrisStrawOne HundredThirteen

(71) Applicant: Driscoll's, Inc., Watsonville, CA (US)

(72) Inventors: Philip J. Stewart, Royal Oaks, CA (US); Esra Alwan, Seaside, CA (US); Debora Liabeuf, Watsonville, CA (US); Amy M. Edmondson, Royal Oaks, CA (US); Iana Kostina, Salinas, CA (US)

(73) Assignee: Driscoll's, Inc., Watsonville, CA (US)

( * ) Notice: Subject to any disclaimer, the term of this patent is extended or adjusted under 35 U.S.C. 154(b) by 0 days.

(21) Appl. No.: 19/385,933

(22) Filed: Nov. 11, 2025

(51) Int. Cl.
*A01H 5/08* (2018.01)

(52) U.S. Cl.
USPC ..... Plt./209

(58) Field of Classification Search
USPC ..... Plt./156, 208, 209
See application file for complete search history.

(56) References Cited

U.S. PATENT DOCUMENTS

PP5,300 P 10/1984 Johnson, Jr. et al.
PP5,840 P 12/1986 Johnson, Jr. et al.
PP6,191 P 5/1988 Johnson, Jr. et al.
PP6,231 P 7/1988 Johnson, Jr. et al.
PP7,024 P 9/1989 Johnson, Jr. et al.
PP7,522 P 5/1991 Johnson, Jr. et al.
PP8,649 P 3/1994 Sjulin et al.
PP8,745 P 5/1994 Sjulin et al.
PP9,130 P 5/1995 Sjulin et al.
PP10,221 P 2/1998 Sjulin et al.
PP10,534 P 8/1998 Sjulin et al.
PP10,642 P 10/1998 Amorao et al.
PP11,035 P 8/1999 Mowrey et al.
PP11,277 P 3/2000 Gilford et al.
PP11,279 P 3/2000 Gilford et al.
PP11,522 P 9/2000 Amorao et al.
PP11,548 P 10/2000 Amorao et al.
PP11,554 P 10/2000 Sjulin et al.
PP11,639 P 11/2000 Mowrey et al.
PP12,186 P2 11/2001 Gilford et al.
PP12,436 P2 3/2002 Amorao et al.
PP12,577 P2 4/2002 Amorao et al.
PP12,817 P2 7/2002 Gilford et al.
PP12,899 P2 9/2002 Mowrey et al.
PP13,386 P2 12/2002 Mowrey et al.
PP14,005 P3 7/2003 Amorao et al.
PP14,062 P3 8/2003 Amorao et al.
PP14,109 P3 8/2003 Gilford et al.
PP14,771 P3 5/2004 Amorao et al.
PP15,145 P2 9/2004 Mowrey et al.
PP15,308 P2 11/2004 Sjulin et al.
PP15,375 P2 11/2004 Mowrey et al.
PP15,435 P2 12/2004 Sjulin et al.
PP15,596 P2 3/2005 Amorao et al.
PP15,731 P2 4/2005 Amorao et al.
PP15,752 P2 5/2005 Gilford et al.
PP16,070 P2 10/2005 Gilford et al.
PP16,238 P2 2/2006 Amorao et al.
PP16,241 P2 2/2006 Mowrey et al.
PP16,298 P2 2/2006 Gilford et al.
PP16,299 P2 2/2006 Gilford et al.
PP16,475 P2 4/2006 Gilford et al.
PP18,040 P3 9/2007 Mowrey et al.
PP18,041 P3 9/2007 Gilford
PP18,458 P2 1/2008 Ferguson et al.
PP18,575 P3 3/2008 Amorao et al.
PP18,878 P2 6/2008 Mowrey et al.
PP19,240 P2 9/2008 Gilford et al.
PP19,673 P3 2/2009 Ferguson et al.
PP20,248 P3 9/2009 Rogers et al.
PP20,701 P2 2/2010 Gilford et al.
PP20,731 P2 2/2010 Mowrey et al.
PP20,733 P2 2/2010 Mowrey et al.
PP20,735 P2 2/2010 Ferguson
PP20,775 P2 2/2010 Mowrey et al.
PP20,922 P2 4/2010 Gilford et al.
PP21,538 P2 11/2010 Gilford et al.
PP21,559 P2 12/2010 Ferguson et al.
PP21,762 P2 3/2011 Stewart et al.
PP22,040 P3 7/2011 Stewart et al.
PP22,218 P2 11/2011 Ferguson et al.
PP22,247 P2 11/2011 Ferguson
PP23,107 P2 10/2012 Ferguson et al.
PP23,148 P2 10/2012 Gilford et al.
PP23,377 P2 2/2013 Ferguson et al.
PP23,378 P2 2/2013 Pullen et al.
PP23,382 P2 2/2013 Ferguson et al.
PP23,383 P2 2/2013 Ferguson et al.
PP23,400 P2 2/2013 Ferguson et al.
PP23,401 P2 2/2013 Pullen et al.
PP23,459 P2 3/2013 Stewart et al.
PP23,506 P3 4/2013 Ferguson et al.
PP23,517 P3 4/2013 Ferguson et al.
PP24,096 P3 12/2013 Fear et al.
PP24,317 P3 3/2014 Ferguson et al.
PP24,333 P3 3/2014 Vitten et al.
PP24,395 P3 4/2014 Vitten et al.
PP24,533 P3 6/2014 Ferguson et al.
PP24,745 P2 8/2014 Vitten et al.
PP25,408 P3 4/2015 Vitten et al.
PP25,437 P3 4/2015 Vitten et al.

(Continued)

*Primary Examiner* — Karen M Redden

(74) *Attorney, Agent, or Firm* — Morrison & Foerster LLP

(57) ABSTRACT

A new and distinct variety of strawberry plant named 'DrisStrawOneHundredThirteen', particularly selected for its large fruit. sustained production, and fruit quality and flavor, is disclosed.

6 Drawing Sheets

(56) References Cited

U.S. PATENT DOCUMENTS

| | | | |
|---|---|---|---|
| PP25,698 | P3 | 7/2015 | Ferguson et al. |
| PP25,699 | P3 | 7/2015 | Stewart et al. |
| PP25,747 | P3 | 7/2015 | Kibbe et al. |
| PP25,866 | P3 | 9/2015 | Ferguson et al. |
| PP26,800 | P3 | 6/2016 | Stewart et al. |
| PP26,801 | P3 | 6/2016 | Stewart et al. |
| PP26,802 | P3 | 6/2016 | Rodriguez Alcazar et al. |
| PP27,442 | P2 | 12/2016 | Kibbe et al. |
| PP27,645 | P3 | 2/2017 | Vitten et al. |
| PP27,682 | P3 | 2/2017 | Kibbe et al. |
| PP27,711 | P3 | 2/2017 | Vitten et al. |
| PP27,813 | P3 | 3/2017 | Ferguson et al. |
| PP29,289 | P3 | 5/2018 | Vitten et al. |
| PP29,728 | P2 | 10/2018 | Stewart et al. |
| PP29,729 | P2 | 10/2018 | Kibbe et al. |
| PP29,730 | P2 | 10/2018 | Kibbe et al. |
| PP29,731 | P2 | 10/2018 | Ferguson et al. |
| PP29,747 | P2 | 10/2018 | Vitten et al. |
| PP29,748 | P2 | 10/2018 | Vitten et al. |
| PP29,749 | P2 | 10/2018 | Stewart et al. |
| PP30,775 | P2 | 8/2019 | Carrillo Mendoza et al. |
| PP30,789 | P2 | 8/2019 | Ferguson et al. |
| PP30,818 | P2 | 8/2019 | Pakozdi et al. |
| PP30,851 | P2 | 8/2019 | Fear et al. |
| PP30,936 | P2 | 10/2019 | Stewart et al. |
| PP31,083 | P2 | 11/2019 | Carrillo Mendoza et al. |
| PP31,233 | P2 | 12/2019 | Pakozdi et al. |
| PP31,527 | P3 | 3/2020 | Carrillo Mendoza et al. |
| PP31,655 | P2 | 4/2020 | Carrillo Mendoza et al. |
| PP31,703 | P2 | 4/2020 | Stewart et al. |
| PP31,827 | P2 | 6/2020 | Ferguson et al. |
| PP31,896 | P2 | 6/2020 | Pakozdi et al. |
| PP31,935 | P2 | 7/2020 | Pakozdi et al. |
| PP32,079 | P2 | 8/2020 | Carrillo Mendoza et al. |
| PP32,080 | P2 | 8/2020 | Ferguson et al. |
| PP32,271 | P2 | 10/2020 | Ferguson et al. |
| PP32,305 | P3 | 10/2020 | Pakozdi et al. |
| PP32,498 | P2 | 11/2020 | Mendoza et al. |
| PP32,499 | P3 | 11/2020 | Jacobs et al. |
| PP32,500 | P3 | 11/2020 | Stewart et al. |
| PP32,801 | P2 | 2/2021 | Ferguson et al. |
| PP32,814 | P2 * | 2/2021 | Stewart ..... A01H 5/08 Plt./209 |
| PP32,824 | P2 | 2/2021 | Stewart et al. |
| PP33,070 | P2 | 5/2021 | Mendoza et al. |
| PP33,090 | P2 | 5/2021 | Mendoza et al. |
| PP33,283 | P2 | 7/2021 | Stewart et al. |
| PP33,513 | P2 | 9/2021 | Stewart et al. |
| PP33,737 | P2 | 12/2021 | Hernandez et al. |
| PP33,738 | P2 | 12/2021 | Stewart et al. |
| PP34,072 | P2 | 3/2022 | Mendoza et al. |
| PP34,212 | P2 | 5/2022 | Jacobs et al. |
| PP34,241 | P2 | 5/2022 | Pakozdi et al. |
| PP34,273 | P2 | 5/2022 | Mendoza et al. |
| PP34,274 | P2 | 5/2022 | Ferguson et al. |
| PP34,440 | P2 | 7/2022 | Nguyen et al. |
| PP34,441 | P2 | 7/2022 | Nguyen et al. |
| PP34,659 | P2 | 10/2022 | Nguyen et al. |
| PP34,751 | P2 | 11/2022 | Mendoza et al. |
| PP34,775 | P2 | 11/2022 | Stewart et al. |
| PP34,776 | P2 | 11/2022 | Nguyen et al. |
| PP34,777 | P2 | 11/2022 | Mendoza et al. |
| PP34,916 | P2 | 1/2023 | Stewart et al. |
| PP35,092 | P2 | 4/2023 | Nguyen et al. |
| PP35,093 | P2 | 4/2023 | Stewart et al. |
| PP35,158 | P2 | 5/2023 | Stewart et al. |
| PP35,909 | P2 | 7/2024 | Lillo et al. |
| PP36,413 | P2 | 1/2025 | Nguyen |
| PP36,485 | P2 | 2/2025 | Coons et al. |
| PP36,665 | P2 | 5/2025 | Hernandez et al. |
| PP36,666 | P2 | 5/2025 | Hernandez et al. |
| PP36,756 | P2 | 6/2025 | Stewart et al. |
| PP36,911 | P2 | 9/2025 | Palmer et al. |

* cited by examiner

STRAWBERRY PLANT NAMED 'DrisStrawOneHundredThirteen'

Latin name: Botanical classification: *Fragaria* x *ananassa.*

Varietal denomination: The varietal denomination of the claimed variety of strawberry plant is 'DrisStrawOneHundredThirteen'.

BACKGROUND OF THE INVENTION

Cultivated strawberry is a hybrid species of the genus *Fragaria* that is grown worldwide for its fruit. Modern strawberry was first bred in Brittany, France, in the 18$^{th}$ century by crossing *Fragaria virginiana* with *Fragaria chiloensis*. Strawberry fruit is an aggregate accessory fruit, with the fleshy part of the fruit being derived from the receptacle that holds the ovaries.

Strawberry varieties vary widely in color, size, shape, flavor, season of ripening, degree of fertility, and susceptibility to disease. Certain varieties vary in foliage, and some vary in the relative development of their reproductive organs. Typically, strawberry flowers appear hermaphroditic in structure, but function as either male or female. Generally, commercial production of strawberry plants involves propagation from runners and distribution as either plugs or bare root plants. Cultivation is either perennial or annual plasticulture. During the off season, strawberries can also be produced in greenhouses.

Strawberry fruit is widely appreciated for its characteristic bright red color, aroma, juicy texture, and sweetness. Strawberry fruit is a popular fruit that is generally consumed either fresh or in prepared foods, such as preserves and baked goods.

Strawberry is an important and valuable fruit crop. Accordingly, there is a need for new varieties of strawberry plants. In particular, there is a need for improved varieties of strawberry plant that are stable, high yielding, and agronomically sound.

SUMMARY OF THE INVENTION

In order to meet these needs, the present invention is directed to an improved variety of strawberry plant. In particular, the invention relates to a new and distinct variety of strawberry plant (*Fragaria* x *ananassa*), which has been denominated as 'DrisStrawOneHundredThirteen'.

Strawberry plant variety 'DrisStrawOneHundredThirteen' originated from a controlled cross between the female parent 'DrisStrawEighty' (U.S. Plant Pat. No. 32,824) and the proprietary strawberry male parent '113AC 72' (unpatented). Progeny plants from this cross, including 'DrisStrawOneHundredThirteen', were asexually propagated via stolons in Shasta County, California in May 2019. Strawberry plant variety 'DrisStrawOneHundredThirteen' was later specifically identified and selected in Monterey County, California in May 2020.

'DrisStrawOneHundredThirteen' was subsequently asexually propagated via stolons, and has undergone testing at test plots in Monterey County, California for five years (2020 to 2025). The present variety has been found to be stable and reproduce true to type through successive asexual propagations via stolons and tissue culture.

'DrisStrawOneHundredThirteen' was particularly selected for its large fruit, sustained production, and fruit quality and flavor.

DESCRIPTION OF THE DRAWINGS

This new strawberry plant is illustrated by the accompanying photographs. The colors shown are as true as can be reasonably obtained by conventional photographic procedures. Unless otherwise indicated, the photographs are of plants that are approximately 10 months old after planting.

DETAILED BOTANICAL DESCRIPTION

Figure 1:
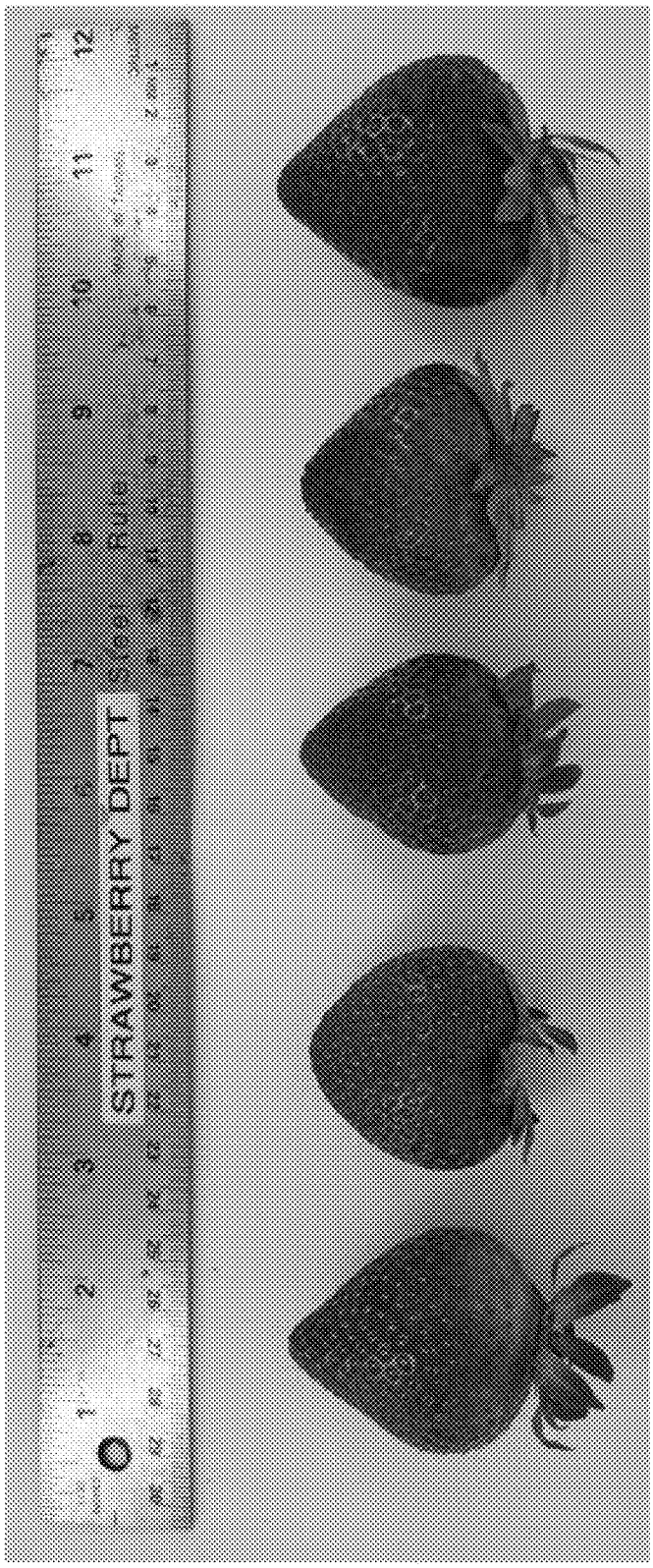
FIG. 1 illustrates whole fruit of variety 'DrisStrawOneHundredThirteen'.
Figure 2:
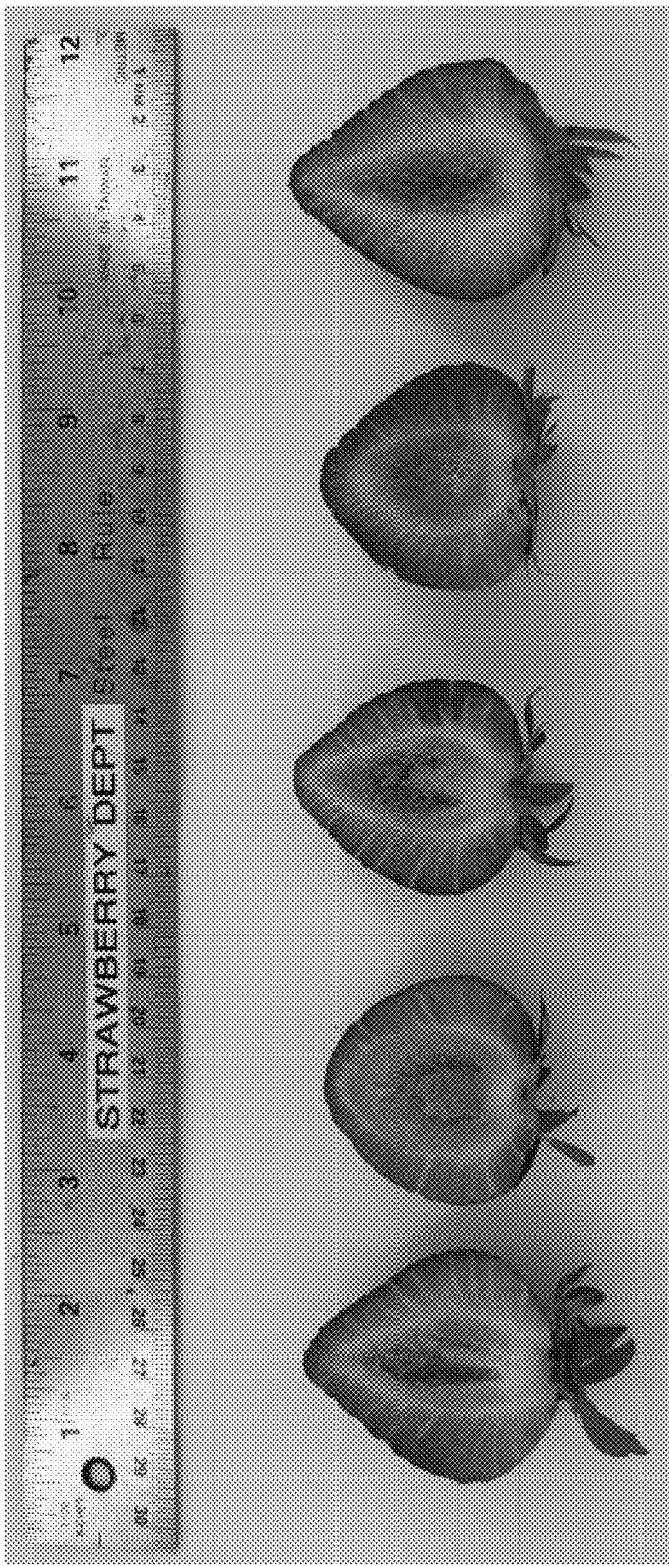
FIG. 2 illustrates longitudinal sections of fruit of variety 'DrisStrawOneHundredThirteen'.
Figure 3:
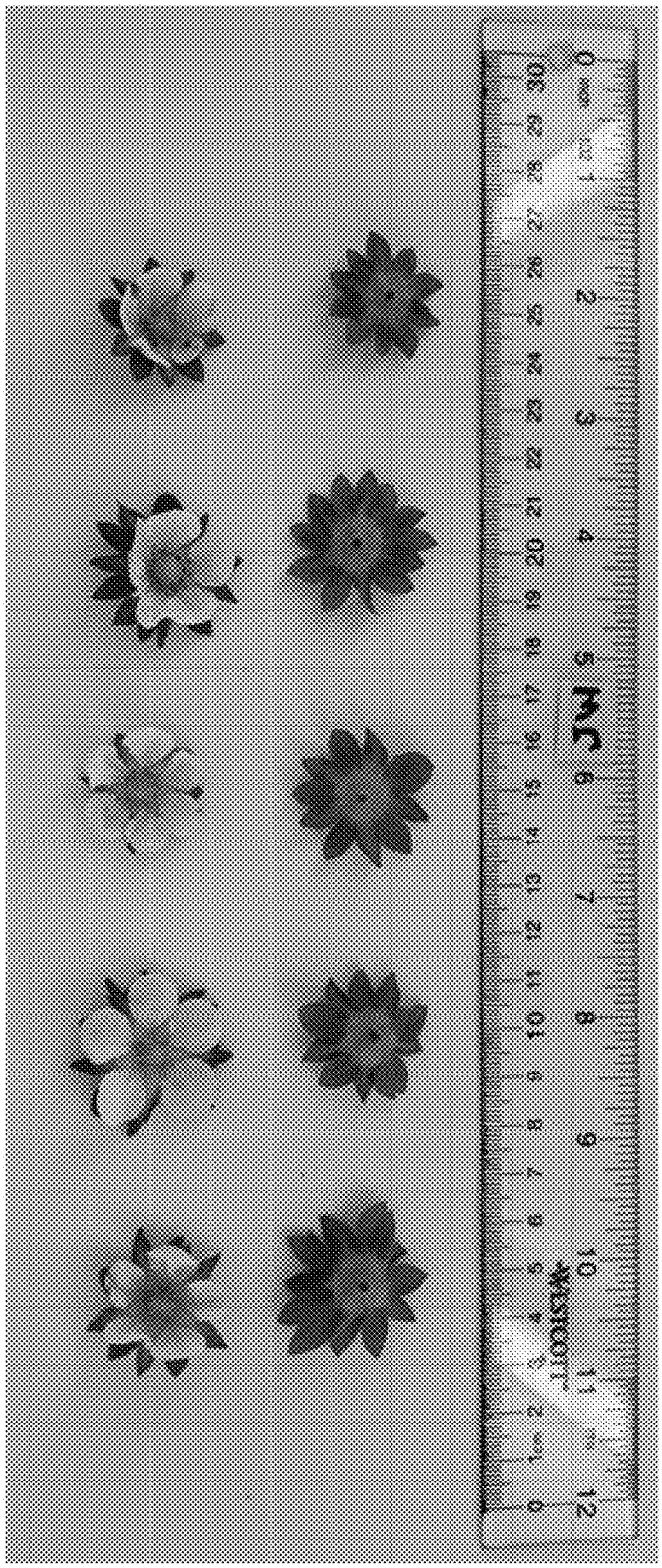
FIG. 3 illustrates the upper surface (top row) and lower surface (bottom row) of flowers of variety 'DrisStrawOneHundredThirteen'.
Figure 4:
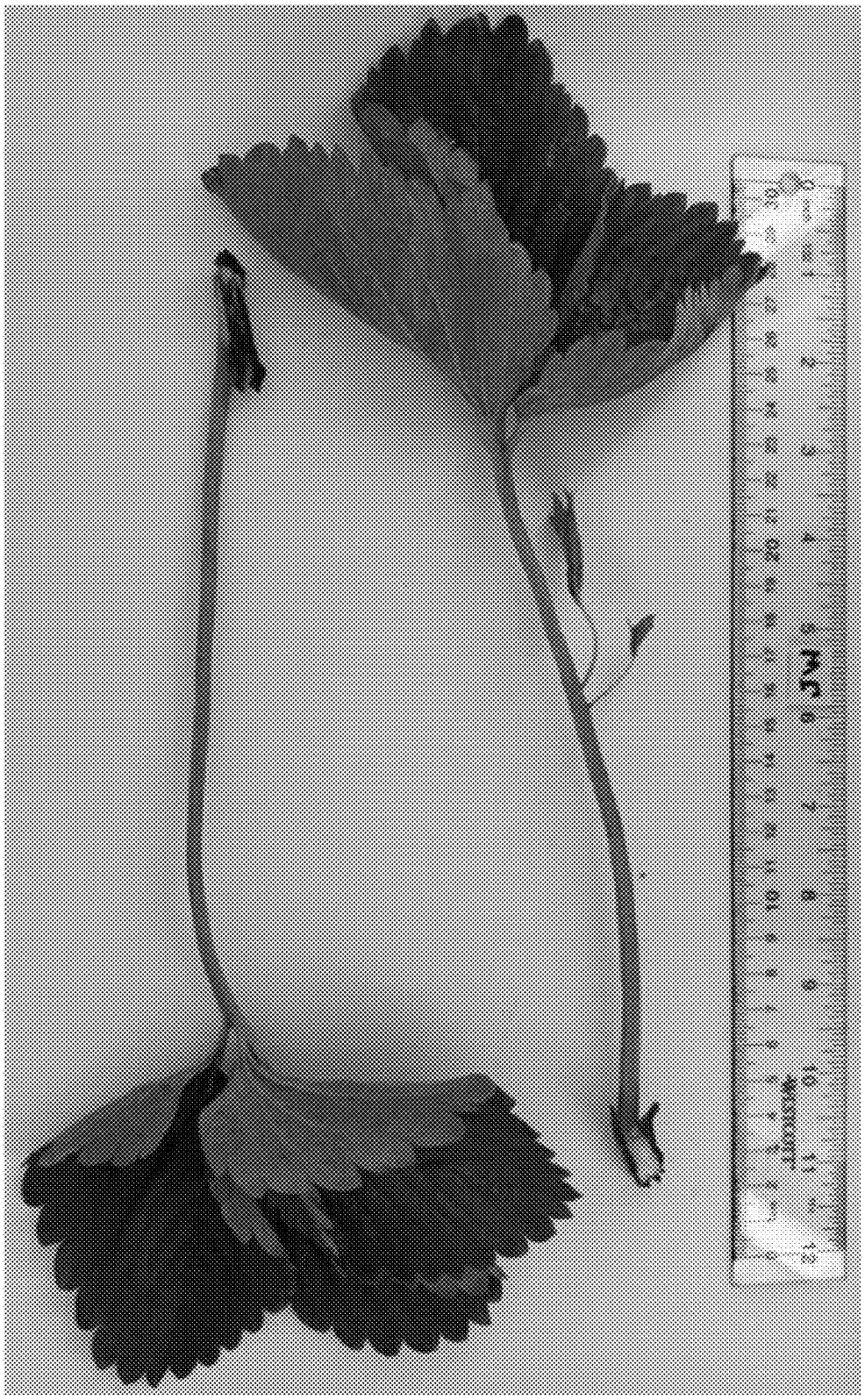
FIG. 4 illustrates the leaves of variety 'DrisStrawOneHundredThirteen'.
Figure 5:
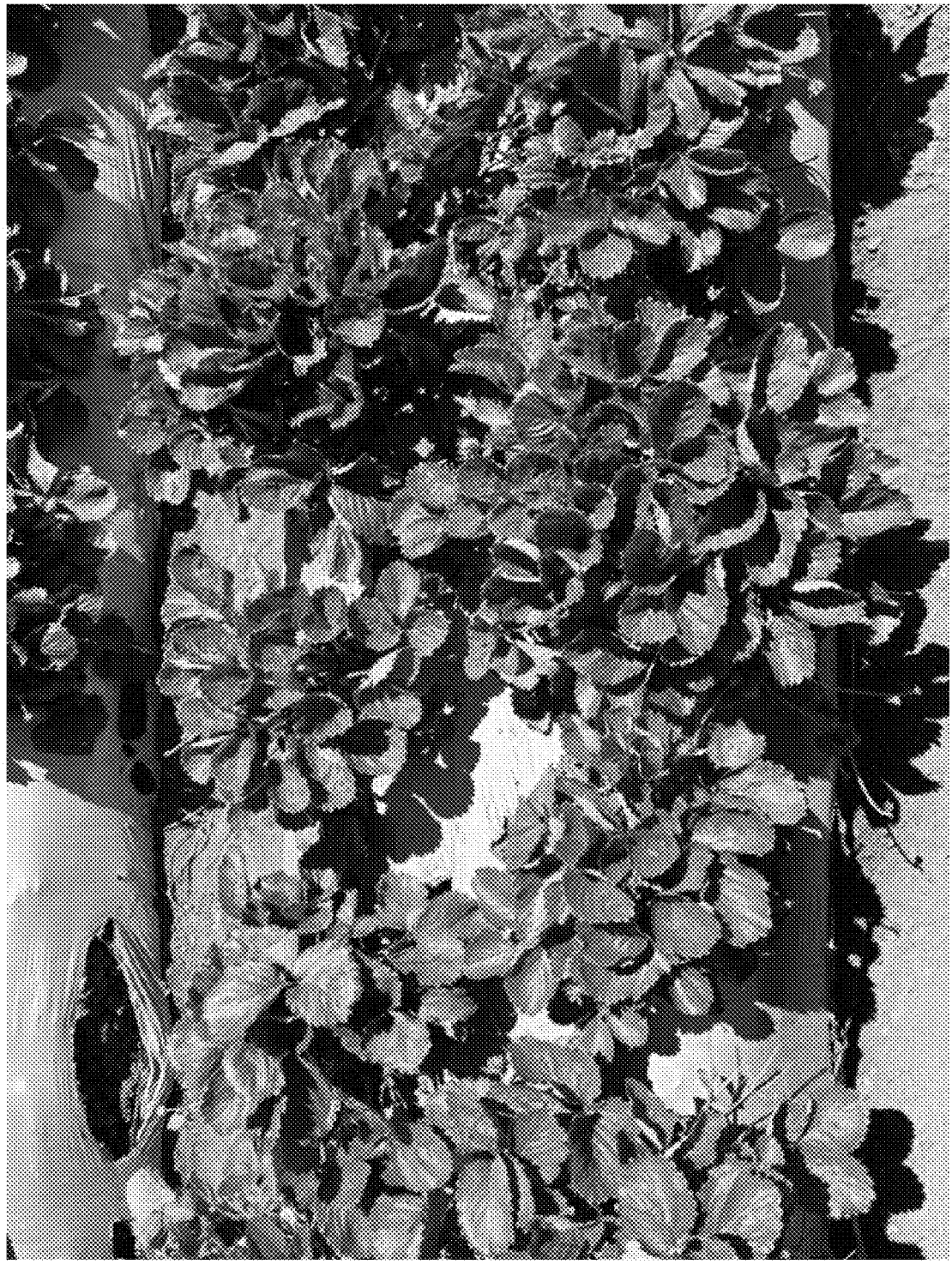
FIG. 5 illustrates whole plants of variety 'DrisStrawOneHundredThirteen'.
Figure 6:
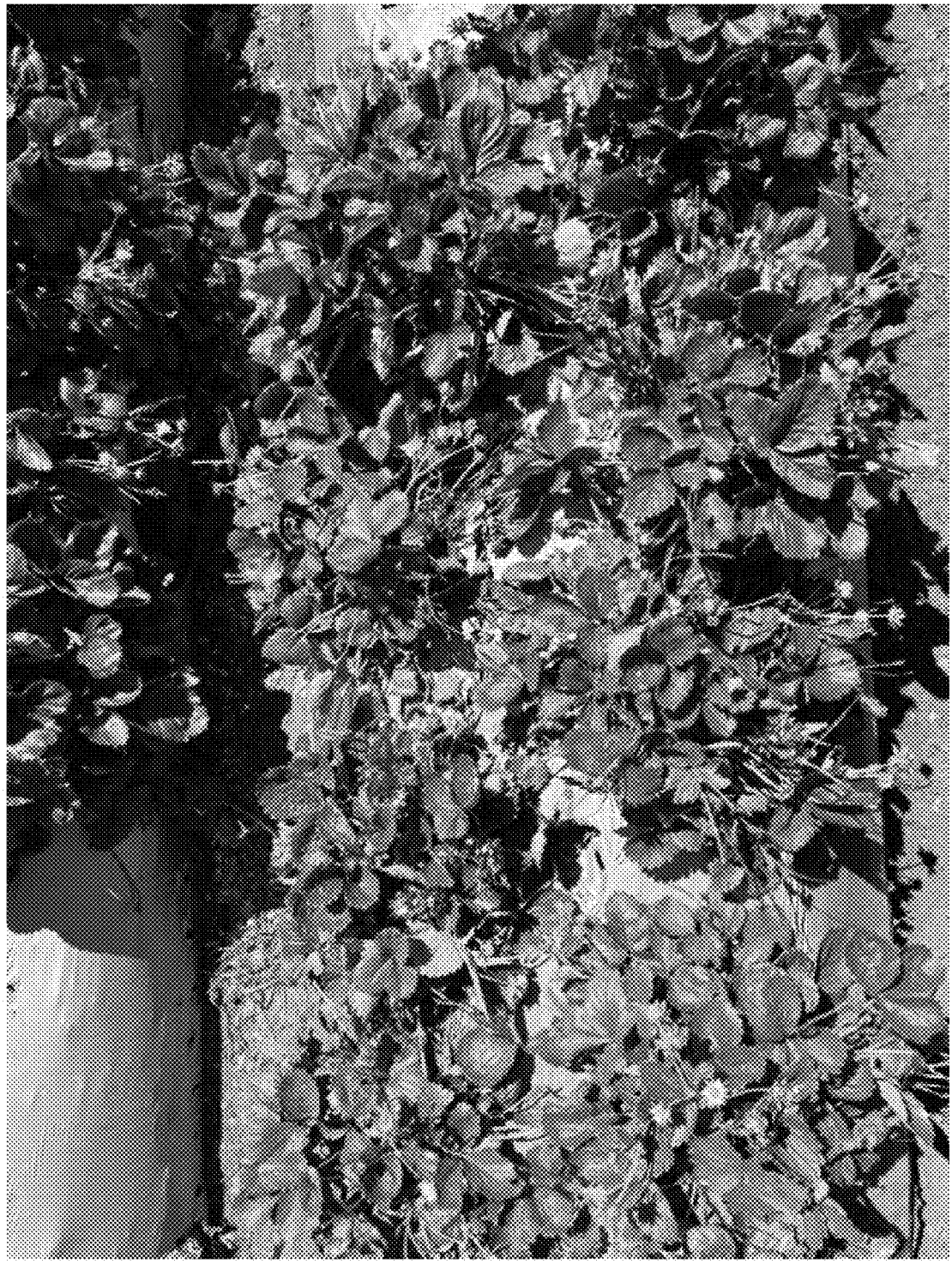
FIG. 6 illustrates another view of whole plants of variety 'DrisStrawOneHundredThirteen'.

The following detailed descriptions set forth the distinctive characteristics of 'DrisStrawOneHundredThirteen'. The data which define these characteristics is based on observations taken in Monterey County, California from 2020 to 2025. This description is in accordance with UPOV terminology. Color designations, color descriptions, and other phenotypical descriptions may deviate from the stated values and descriptions depending upon variation in environmental, seasonal, climatic, and cultural conditions.

'DrisStrawOneHundredThirteen' has not been observed under all possible environmental conditions. The botanical description of 'DrisStrawOneHundredThirteen' was taken from plants that were approximately ten months old after planting. The indicated values represent averages calculated from measurements of several plants. Color references are primarily to The R.H.S. Colour Chart of The Royal Horticultural Society of London (R.H.S.) (2015 edition). Descriptive terminology follows the *Plant Identification Terminology, An Illustrated Glossary,* 2$^{nd}$ edition by James G. Harris and Melinda Woolf Harris, unless where otherwise defined.

Classification:

*Species.*—*Fragaria* x *ananassa.*

*Common name.*—Strawberry.

*Denomination.*—'DrisStrawOneHundredThirteen'.

Parentage:

*Female parent.*—'DrisStrawEighty' (U.S. Plant Pat. No. 32,824).

*Male parent.*—Proprietary strawberry plant '113AC 72' (unpatented).

Plant:

*Height.*—24.3 cm.

*Width.*—44 cm.

*Height/width ratio.*—0.6.

*Number of crowns per plant.*—5.5.

*Growth habit.*—Semi-upright.

*Density of foliage.*—Dense.

*Vigor.*—Medium.

Stolon:

*Average number of daughter plants per mother.*—96.

*Diameter (at bract).*—3.5 mm.

*Overall color.*—RHS N144A (Strong yellowish green).

*Anthocyanin coloration.*—Weak.

*Anthocyanin color.*—RHS 179B (Moderate red).

*Density of pubescence.*—Sparse.

Fruiting truss:

*Length (from crown to base of terminal flower or fruit)*.—25.2 cm.

*Diameter (at base of truss)*.—0.48 cm.

*Number of berries per truss*.—4.8.

*Attitude at first picking*.—Semi-erect.

*Color (at base of truss)*.—RHS N144A (Strong yellowish green).

Leaf:

*Number of leaflets*.—Three only.

*Color of leaf upper surface*.—RHS NN137A (Greyish olive green).

*Color of leaf lower surface*.—RHS 147B (Moderate yellow green).

*Rugosity*.—Weak.

*Glossiness*.—Medium.

*Variegation*.—Absent.

*Terminal leaflet*.—Length: 9 cm. Width: 8.7 cm. Length/width ratio: 1.04.Number of teeth per terminal leaflet: 25.9. Overall shape: Orbicular. Shape of base: Rounded. Shape of apex: Rounded. Margin: Serrate to crenate. Margin profile: Flat (level with the leaflet blade). Depth of incisions of margin: Medium deep. Profile in cross-section: Concave.

*Petiole*.—Length: 200.2 mm. Diameter: 4.0 mm. Overall color: RHS 145A (Strong yellow green). Pubescence: Medium. Attitude of hairs: Horizontal. Bract frequency (number present on each petiole): 0.4.

*Petiolule*.—Length: 12.8 mm. Diameter: 1.9 mm. Color: RHS 145A (Strong yellow green).

*Stipule*.—Length: 27.1 mm. Width: 14.9 mm. Stipule color: RHS 145B (Light yellow green). Anthocyanin coloration: Weak. Anthocyanin color: RHS 73A (Deep purplish pink). Pubescence: Medium.

Inflorescence:

*Number of flowers per plant*.—8.7.

*Position of inflorescence in relation to foliage*.—Same level.

*Flowering interval*.—February to October.

*Flowering runners*.—Absent.

*Pedicel*.—Attitude of hairs: Upwards.

*Flower*.—Flower diameter (petal tip to petal tip on non-flattened flower): 27.8 mm. Arrangement of petals: Touching. Size of calyx in relation to corolla: Larger. Receptacle color: RHS 150A (Brilliant yellow green). Stamen: Present. Anther color: RHS 12A (Vivid yellow).

*Petal*.—Length: 7.8 mm. Width: 7.3 mm. Length/width ratio: 1.1. Number of petals per flower: 5.6. Color of upper surface: RHS 155C (Greenish white). Color of lower surface: RHS 155C (Greenish white). Overall shape: Orbicular/circular. Shape of apex: Rounded. Margin: Entire. Shape of base: Concavo-convex.

*Calyx*.—Diameter (sepal tip to sepal tip, measured on back of flower): 40.7 mm.

*Sepal*.—Length: 16.2 mm. Width: 8.3 mm. Number of sepals per flower: 11.3. Overall shape: Elliptical. Margin: Entire.

Fruit:

*Fruit size*.—Length: 44.8 mm. Width: 40.7 mm. Length/width ratio: 1.1.

*Fruit hollow*.—Length: 21.5 mm. Width: 9.6 mm. Length/width ratio: 2.2.

*Shape*.—Conical.

*Difference in shape of terminal and other fruits*.—None or very slight.

*Position of maximum width*.—Moderately towards calyx.

*Shape of apex*.—Rounded.

*Shape at calyx end*.—Rounded.

*Fruit color*.—RHS N45A (Moderate red).

*Evenness of color*.—Slightly uneven.

*Evenness of surface*.—Even or very slightly uneven.

*Glossiness*.—Medium.

*Width of band without achenes*.—Absent or very narrow.

*Position of achenes*.—Level with surface.

*Position of calyx attachment*.—Level with fruit.

*Attitude of sepals*.—Outwards.

*Diameter of calyx in relation to diameter of fruit*.—Slightly smaller.

*Adherence of calyx*.—Medium.

*Firmness*.—Medium firm.

*Color of flesh (excluding core)*.—RHS 40A (Vivid reddish orange).

*Evenness of color of the flesh*.—Even.

*Distribution of flesh color*.—Marginal and central.

*Color of core*.—RHS 36B (Light yellowish pink).

*Sweetness/soluble solids (in ° Brix)*.—8.7.

*Titratable acidity (% as citric acid)*.—0.76%.

*Individual fruit weight*.—28.6 g/fruit.

*Achenes*.—Number of achenes per fruit: 196. Density of achenes: Medium dense. Weight: 0.63 mg/achene. Color of upper (sunward) side of berry: RHS 43A (Vivid reddish orange). Color of lower (shaded) side of berry: RHS 1A (Brilliant greenish yellow).

*Fruiting*.—Harvest interval: March to October. Chilling requirement: ~680-880 chill hours at cold-room temperatures (~0-2° C.). Type of bearing: Day neutral under 30° C. and 12- to 18-hour day length. Productivity: 61,001 kg to 93,937 kg of fruit per hectare per season from 5- to 12-month-old plants after planting when grown in Monterey County, California.

Resistance to abiotic stress, pests, and diseases:

*Macrophomina crown rot (Macrophomina phaseolina)*.—Susceptible.

*Verticillium wilt (Verticillium sp.)*.—Moderately resistant.

*Anthracnose crown rot (Colletotrichum acutatum)*.—Moderately resistant.

*Phytophthora crown wilt (Phytophthora cactorum)*.—Moderately resistant.

*Fusarium wilt race* 1 *(Fusarium oxysporum)*.—Resistant.

*Powdery mildew (Podosphaera macularis)*.—Moderately resistant on fruit, moderately susceptible on foliar tissue.

COMPARISON WITH PARENTAL AND REFERENCE VARIETIES

'DrisStrawOneHundredThirteen' differs from the female parent 'DrisStrawEighty' (U.S. Plant Pat. No. 32,824) in that 'DrisStrawOneHundredThirteen' has medium plant vigor, weak stolon anthocyanin coloration, rounded shape of base on terminal leaflet, and day neutral type of bearing, whereas 'DrisStrawEighty' has strong plant vigor, medium stolon anthocyanin coloration, obtuse shape of base on terminal leaflet, and partially remontant type of bearing. Additionally, 'DrisStrawOneHundredThirteen' has a larger fruit size than 'DrisStrawEighty'.

'DrisStrawOneHundredThirteen' differs from the male parent proprietary strawberry plant '113AC 72' (unpatented) in that 'DrisStrawOneHundredThirteen' has greater plant vigor, a denser canopy, and larger fruit size than '113AC 72'.

'DrisStrawOneHundredThirteen' differs from the reference variety 'DrisStrawEightyOne' (U.S. Plant Pat. No. 32,814) in that 'DrisStrawOneHundredThirteen' has a large fruit size, weak stolon anthocyanin coloration, large fruit size, slightly smaller diameter of calyx in relation to fruit diameter, and day neutral type of bearing, whereas 'DrisStrawEightyOne' has a medium fruit size, absent or very weak stolon anthocyanin coloration, medium fruit size, slightly larger diameter of calyx in relation to fruit diameter, and partially remontant type of bearing.

'DrisStrawOneHundredThirteen' differs from the reference variety 'DrisStrawOneHundredThree' (U.S. Plant Pat. No. 35,093) in that 'DrisStrawOneHundredThirteen' has a large fruit size, weak stolon anthocyanin coloration, rounded shape of terminal leaflet base, upwards attitude of pedicel hairs, conical fruit shape, and the position of calyx attachment is level with fruit, whereas 'DrisStrawOneHundredThree' has a medium fruit size, strong stolon anthocyanin coloration, acute shape of terminal leaflet base, horizontal attitude of pedicel hairs, cordate fruit shape, and inserted position of calyx attachment.

We claim:

1. A new and distinct variety of strawberry plant named 'DrisStrawOneHundredThirteen' as shown and described herein.

* * * * *